US011339272B2

United States Patent
Hamatani et al.

(10) Patent No.: US 11,339,272 B2
(45) Date of Patent: May 24, 2022

(54) ADDITIVE FOR RUBBER, RUBBER COMPOSITION, AND TIRE USING THE SAME

(71) Applicants: BRIDGESTONE CORPORATION, Tokyo (JP); OTSUKA CHEMICAL CO., LTD., Osaka (JP)

(72) Inventors: Satoshi Hamatani, Higashimurayama (JP); Shinya Shinozaki, Tokushima (JP); Mifuyu Ueno, Tokushima (JP); Masaki Abe, Tokushima (JP)

(73) Assignees: BRIDGESTONE CORPORATION, Tokyo (JP); OTSUKA CHEMICAL CO., LTD., Osaka (JP)

( * ) Notice: Subject to any disclaimer, the term of this patent is extended or adjusted under 35 U.S.C. 154(b) by 180 days.

(21) Appl. No.: 16/464,508

(22) PCT Filed: Nov. 29, 2017

(86) PCT No.: PCT/JP2017/042920
§ 371 (c)(1),
(2) Date: May 28, 2019

(87) PCT Pub. No.: WO2018/101368
PCT Pub. Date: Jun. 7, 2018

(65) Prior Publication Data
US 2021/0108048 A1    Apr. 15, 2021

(30) Foreign Application Priority Data
Nov. 30, 2016   (JP) ............... JP2016-233610

(51) Int. Cl.
| C08K 5/30 | (2006.01) |
| B60C 1/00 | (2006.01) |
| B60C 11/00 | (2006.01) |
| C07C 243/38 | (2006.01) |
| C08K 3/04 | (2006.01) |
| C08L 7/00 | (2006.01) |
| C08L 9/00 | (2006.01) |

(52) U.S. Cl.
CPC .............. *C08K 5/30* (2013.01); *B60C 1/0016* (2013.01); *B60C 11/0008* (2013.01); *C07C 243/38* (2013.01); *C08K 3/04* (2013.01); *C08L 7/00* (2013.01); *C08L 9/00* (2013.01); *B60C 2011/0025* (2013.01)

(58) Field of Classification Search
CPC .......... C08K 5/30; C08K 3/04; B60C 1/0016; C07C 243/38; C08L 7/00; C08L 9/00
USPC ....................................................... 524/194
See application file for complete search history.

(56) References Cited

U.S. PATENT DOCUMENTS

| 3,689,554 A | * | 9/1972 | Ley | .......................... | C08K 5/30 |
| | | | | | 564/148 |
| 6,380,288 B1 | * | 4/2002 | Hojo | ......................... | B60C 1/00 |
| | | | | | 152/450 |

(Continued)

FOREIGN PATENT DOCUMENTS

| CN | 1095077 A | 11/1994 |
| CN | 101160353 A | 4/2008 |

(Continued)

OTHER PUBLICATIONS

Fujikawa et al "Yakugaku Zasshi Journal of the Pharmaceutical Society of Japan", vol. 78, issue 5 Studies on Chemotherapeutics for *Mycobacterium* tuberculosis. XL. Synthesis and Antibacterial Activity on *Mycobacterium* tuberculosis of p-Aminosalicyloyl hydrazone. (Year: 1958).*

(Continued)

*Primary Examiner* — Doris L Lee
(74) *Attorney, Agent, or Firm* — Sughrue Mion, PLLC

(57) ABSTRACT

An additive for rubber that enables a rubber composition to have excellent low heat generating property and processability, a rubber composition containing the additive for rubber, and a tire using the same are provided. A rubber composition comprises a hydrazone compound represented by the following Formula (I):

$$A-\overset{\overset{\displaystyle O}{\|}}{C}-NH-N=C\overset{\displaystyle R^1}{\underset{\displaystyle R^2}{}} \quad (1)$$

where $R^1$ and $R^2$ each independently represent a hydrogen atom, an alkyl group with a carbon number of 1 to 16, or an alkenyl group with a carbon number of 2 to 6, and A represents a group represented by the following Formula (A-1) or Formula (A-2):

(A-1)

(A-2)

(Continued)

12 Claims, No Drawings

(56) References Cited

U.S. PATENT DOCUMENTS

| | | | |
|---|---|---|---|
| 2002/0019374 A1 | 2/2002 | Gypser et al. | |
| 2004/0110963 A1* | 6/2004 | Burri .................... | C07C 251/86 548/494 |
| 2013/0289165 A1 | 10/2013 | De Landtsheer et al. | |
| 2013/0331480 A1 | 12/2013 | Suzuki et al. | |
| 2016/0017121 A1 | 1/2016 | Saiki et al. | |

FOREIGN PATENT DOCUMENTS

| | | |
|---|---|---|
| CN | 103391967 A | 11/2013 |
| CN | 105073844 A | 11/2015 |
| CN | 105130856 A | 12/2015 |
| EP | 0 613 924 A1 | 9/1994 |
| EP | 1 854 839 A1 | 11/2007 |
| JP | 11-292834 A | 10/1999 |
| JP | 2002-030058 A | 1/2002 |
| JP | 2014-501827 A | 1/2014 |

OTHER PUBLICATIONS

International Preliminary Report on Patentability with the translation of Written opinion dated Jun. 4, 2019 by issued by the International Bureau in International Application No. PCT/JP2017/042920.

Communication dated Jun. 22, 2020, from the European Patent Office in application No. 17876534.3.

Offe H A et al.,"Hydrazinderivate und ihre Wirksamkeit gegenuber *Mycobacterium tuberculosis*//The Activity of Hydrazine Derivatives Against *Mycobacterium* Tuberculosis", Zeitschrift Fuer Naturforschung, XPO08041195, vol. 7B, Jan. 1, 1952, pp. 446-462 (17 pages total).

Search Report dated Nov. 10, 2020, issued by the State Intellectual Property Office of P. R. China in application No. 2017800739937.

Fukujiro Fujikawa et al., "Studies on Chemotherapeutics for *Myocobacterium* tuberculosis. XL Synthesis and Antibacterial Activity on *Mycobacterium* tuberculosis of p-Aminosalicyloylhydrazone", Yakugaku Zasshi, 1958, pp. 559-561, vol. 78.

International Search Report of PCT/JP2017/042920 dated Feb. 27, 2018 [PCT/ISA/210].

Search Report dated Jun. 9, 2021 issued by The State Intellectual Property Office of the P.R. of China in English Application No. 2017800739937.

* cited by examiner

ADDITIVE FOR RUBBER, RUBBER COMPOSITION, AND TIRE USING THE SAME

CROSS REFERENCE TO RELATED APPLICATIONS

This application is a National Stage of International Application No. PCT/JP2017/042920, filed Nov. 29, 2017, claiming priority to Japanese Patent Application No. 2016-233610, filed Nov. 30, 2016.

TECHNICAL FIELD

The present disclosure relates to an additive for rubber, a rubber composition, and a tire using the same.

BACKGROUND

The need for fuel-efficient vehicles has been growing in recent years, and tires with low rolling resistance are in demand. Hence, rubber compositions having low tan δ and excellent low heat generating property are desired as rubber compositions used in tire treads and the like.

Techniques developed to achieve low heat generating property for conventional pneumatic tires include increasing the particle diameter of carbon black in a rubber composition, and decreasing the blending quantity of carbon black. However, these techniques also cause a decrease in the wear resistance of the tread rubber or a decrease in the fracture resistance of the rubber such as cutting resistance and chipping resistance.

There is thus the need to develop techniques for improving low heat generating property without decreasing other properties such as strength.

As an example of such techniques, PTL 1 discloses a rubber composition in which an elastomer containing natural rubber is blended with carbon black and a specific hydrazide compound in order to improve chemical interaction between the rubber component and the carbon black.

CITATION LIST

Patent Literature

PTL 1: JP 2014-501827 A

SUMMARY

Technical Problem

However, the technique disclosed in PTL 1 does not provide sufficient low heat generating property, and better low heat generating property is necessary in order to meet the need for fuel-efficient vehicles. Besides, in the case where a hydrazide compound is contained in the rubber composition, the unvulcanized viscosity increases, and the processability of the rubber composition decreases.

It could therefore be helpful to provide an additive for rubber that can improve the low heat generating property and processability of a rubber composition, and a rubber composition having excellent low heat generating property and processability. It could also be helpful to provide a tire having excellent low heat generating property.

Solution to Problem

As a result of conducting extensive studies, we discovered that, by containing a hydrazone compound having a specific structure in a rubber composition, interaction between the rubber component and carbon black can be enhanced as compared with conventional techniques using a hydrazide compound or a hydrazone compound, so that better low heat generating property and processability can be achieved.

That is, an additive for rubber according to the present disclosure comprises a hydrazone compound represented by the following Formula (I):

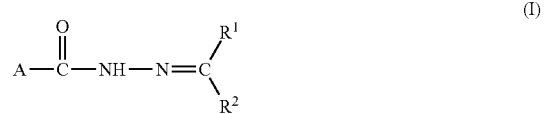

where $R^1$ and $R^2$ each independently represent a hydrogen atom, an alkyl group with a carbon number of 1 to 16, or an alkenyl group with a carbon number of 2 to 6, and A represents a group represented by the following Formula (A-1) or Formula (A-2):

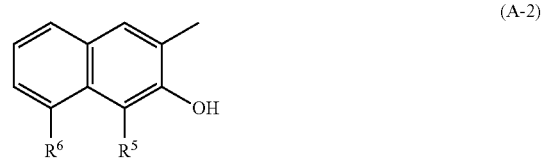

where $R^3$, $R^4$, $R^5$, and $R^6$ each independently represent a hydrogen atom, a hydroxy group, a group of $-N(R^7)(R^8)$, or a nitro group, $R^7$ and $R^8$ each independently represent a hydrogen atom, an alkyl group with a carbon number of 1 to 4, or an acyl group with a carbon number of 1 to 4, not both $R^3$ and $R^4$ are a hydrogen atom, and not both $R^5$ and $R^6$ are a hydrogen atom.

With this structure, the low heat generating property and processability of a rubber composition can be improved.

Preferably, the additive for rubber is for use as a low heat generating agent.

The additive for rubber, when used in a rubber composition, can achieve excellent low heat generating property.

A rubber composition according to the present disclosure comprises: a rubber component containing diene-based rubber; a filler; and the additive for rubber according to the present disclosure.

With this structure, the rubber composition has excellent low heat generating property and processability.

Preferably, in the rubber composition according to the present disclosure, a content of the additive for rubber is 0.05 parts to 30 parts by mass with respect to 100 parts by mass of the rubber component. Thus, better low heat generating property and processability can be achieved.

Preferably, in the rubber composition according to the present disclosure, the diene-based rubber is natural rubber. Thus, better low heat generating property and processability can be achieved.

Preferably, in the rubber composition according to the present disclosure, the filler includes carbon black. Thus, better low heat generating property and processability can be achieved.

Preferably, in the rubber composition according to the present disclosure, a content of the filler is 10 parts to 160 parts by mass with respect to 100 parts by mass of the rubber component. Thus, better low heat generating property and processability can be achieved.

A tire according to the present disclosure comprises the rubber composition described above.

With this structure, the tire has excellent low heat generating property.

A hydrazone compound according to the present disclosure is represented by the following Formula (I):

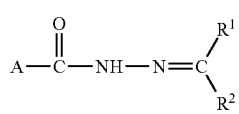

(I)

where $R^1$ and $R^2$ each independently represent a hydrogen atom, an alkyl group with a carbon number of 1 to 16, or an alkenyl group with a carbon number of 2 to 6, and A represents a group represented by the following Formula (A-1) or Formula (A-2):

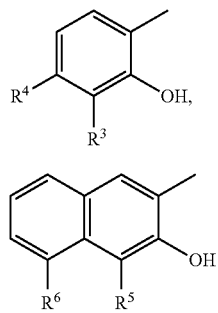

(A-1)

(A-2)

where $R^3$, $R^4$, $R^5$, and $R^6$ each independently represent a hydrogen atom, a hydroxy group, a group of $-N(R^7)(R^8)$, or a nitro group, $R^7$ and $R^8$ each independently represent a hydrogen atom, an alkyl group with a carbon number of 1 to 4, or an acyl group with a carbon number of 1 to 4, not both $R^3$ and $R^4$ are a hydrogen atom, and not both $R^5$ and $R^6$ are a hydrogen atom.

Advantageous Effect

It is thus possible to provide an additive for rubber that can improve the low heat generating property and processability of a rubber composition. It is also possible to provide a rubber composition having excellent low heat generating property and processability. It is further possible to provide a tire having excellent low heat generating property.

DETAILED DESCRIPTION

One of the disclosed embodiments will be described in detail below.
(Additive for Rubber)

An additive for rubber according to the present disclosure contains a hydrazone compound represented by the following Formula (I):

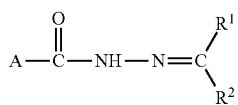

(I)

where $R^1$ and $R^2$ each independently represent a hydrogen atom, an alkyl group with a carbon number of 1 to 16, or an alkenyl group with a carbon number of 2 to 6, and A represents a group represented by the following Formula (A-1) or Formula (A-2):

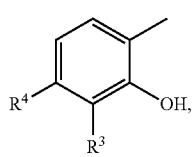

(A-1)

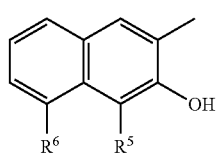

(A-2)

where $R^3$, $R^4$, $R^5$, and $R^6$ each independently represent a hydrogen atom, a hydroxy group, a group of $-N(R^7)(R^8)$, or a nitro group, $R^7$ and $R^8$ each independently represent a hydrogen atom, an alkyl group with a carbon number of 1 to 4, or an acyl group with a carbon number of 1 to 4, not both $R^3$ and $R^4$ are a hydrogen atom, and not both $R^5$ and $R^6$ are a hydrogen atom.

By adding the additive for rubber containing the hydrazone compound represented by the Formula (I) to a diene-based rubber component, excellent low heat generating property and processability can be imparted to the rubber composition.

The additive for rubber according to the present disclosure can be used as a low heat generating agent, a heat generation inhibitor, a heat generation retardant, or a processability improver. In other words, the additive for rubber according to the present disclosure includes a low heat generating agent, a heat generation inhibitor, a heat generation retardant, or a processability improver that contains the hydrazone compound represented by the Formula (I) and that is added to a diene-based rubber component.

Examples of the alkyl group with a carbon number of 1 to 4 for $R^7$ and $R^8$ include straight-chain or branched-chain alkyl groups with a carbon number of 1 to 4 such as methyl group, ethyl group, n-propyl group, isopropyl group, n-butyl group, sec-butyl group, isobutyl group, and tert-butyl group.

Examples of the alkyl group with a carbon number of 1 to 16 for $R^1$ and $R^2$ include, in addition to the examples of the alkyl group with a carbon number of 1 to 4, straight-chain or branched-chain alkyl groups with a carbon number of 1 to 16 such as n-pentyl group, isopentyl group, neopentyl group, tert-pentyl group, n-hexyl group, isohexyl group, heptyl group, octyl group, nonyl group, decyl group, undecyl group, dodecyl group, tridecyl group, tetradecyl group, pentadecyl group, and hexadecyl group. Among them, straight-chain or branched-chain alkyl groups with a carbon number of 1 to 12 are preferable, and straight-chain or branched-chain alkyl groups with a carbon number of 1 to 6 are particularly preferable.

Examples of the alkenyl group with a carbon number of 2 to 6 for $R^1$ and $R^2$ include straight-chain or branched-chain alkenyl groups with a carbon number of 2 to 6 having at least one double bond at any position such as vinyl group, 1-propenyl group, allyl group, isopropenyl group, 2-butenyl group, 3-butenyl group, 1-methyl-2-propenyl group, 3-methyl-2-propenyl group, 1,3-butadienyl group, 1-pentenyl group, 2-pentenyl group, 3-pentenyl group, 4-pentenyl group, 1,1-dimethyl-2-propenyl group, 1-ethyl-2-propenyl group, 1-methyl-2-butenyl group, 1-methyl-3-butenyl group, 1-hexenyl group, 2-hexenyl group, 3-hexenyl group, 4-hexenyl group, 5-hexenyl group, 1,1-dimethyl-2-butenyl group, and 1,1-dimethyl-3-butenyl group.

Among them, straight-chain or branched-chain alkenyl groups with a carbon number of 3 to 5 are preferable, and branched-chain alkenyl groups with a carbon number of 3 to 5 are particularly preferable.

Examples of the acyl group with a carbon number of 1 to 4 for $R^7$ and $R^8$ include straight-chain or branched-chain alkylcarbonyl groups with a carbon number of 1 to 3 such as acetyl group and propionyl group.

Examples of an amino group represented by the group of —N($R^7$)($R^8$) for $R^3$, $R^4$, $R^5$, and $R^6$ include amino group; straight-chain or branched-chain monoalkylamino groups or dialkylamino groups with a carbon number of 1 to 4 such as amino group, methylamino group, dimethylamino group, ethylamino group, methylethylamino group, diethylamino group, n-propylamino group, isopropyl amino group, n-butylamino group, sec-butylamino group, tert-butylamino group, and dibutylamino group; amino groups obtained by mono- or di-substituting straight-chain or branched-chain acyl groups with a carbon number of 1 to 4 such as acetylamino group, bisacetylamino group, propionylamino group, butyrylamino group, and isobutyrylamino group; and amino groups obtained by substituting acyl group with a carbon number of 1 to 4 and alkyl group with a carbon number of 1 to 4 such as acetylmethylamino group.

Herein, with regard to the amino group represented by the group of —N($R^7$)($R^8$), $R^7$ and $R^8$ may integrate together to form a ring. Examples include heterocyclic groups such as aziridinyl group, pyrrolidinyl group, and piperidino group, cyclic amide groups such as 2-oxopiperidino group, and cyclic imide groups such as succinimide group and glutarimide group.

In the additive for rubber according to the present disclosure, at least one of $R^3$ and $R^4$ of the group represented by the Formula (A-1) (hereafter also referred to as "group (A-1)") in the hydrazone compound represented by the Formula (I) is preferably hydroxy group, amino group, or nitro group, and particularly preferably hydroxy group.

In the additive for rubber according to the present disclosure, at least one of $R^5$ and $R^6$ of the group represented by the Formula (A-2) (hereafter also referred to as "group (A-2)") in the hydrazone compound represented by the Formula (I) is preferably hydroxy group, amino group, or nitro group, and particularly preferably hydroxy group.

In the additive for rubber according to the present disclosure, $R^1$ and $R^2$ in the hydrazone compound represented by the Formula (I) are preferably a straight-chain or branched-chain alkyl group with a carbon number of 1 to 14, and particularly preferably a straight-chain or branched-chain alkyl group with a carbon number of 1 to 6.

In the hydrazone compound represented by the Formula (I) in the additive for rubber according to the present disclosure, it is preferable that $R^2$ is isopropyl group when $R^1$ is hydrogen atom, and preferable that $R^2$ is 2-methylpropyl group, undecyl group, or 2-methylpropenyl group when $R^1$ is methyl group. Moreover, it is preferable that any one of $R^1$ and $R^2$ is isopropyl group or undecyl group, and particularly preferable that $R^2$ is 2-methylpropyl group when $R^1$ is methyl group. This imparts better low heat generating property and processability to the rubber composition.

By adding or blending the additive for rubber according to the present disclosure to or with a diene-based rubber component, better low heat generating property and processability can be imparted to the rubber composition.

In the additive for rubber according to the present disclosure, the melting point of the hydrazone compound represented by the Formula (I) is preferably 80° C. or more and less than 250° C., and more preferably 80° C. to 200° C. This increases the affinity for diene-based rubber, and imparts better low heat generating property and processability to the rubber composition.

The following are preferable specific compounds according to the present disclosure:

Compound a

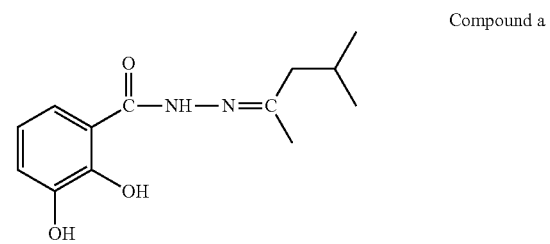

Compound b

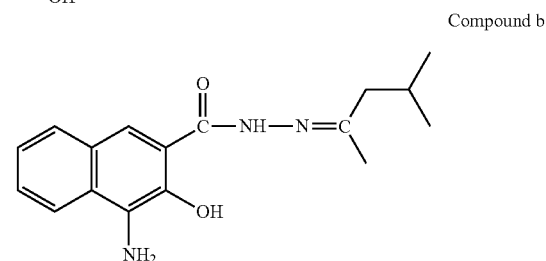

Compound c

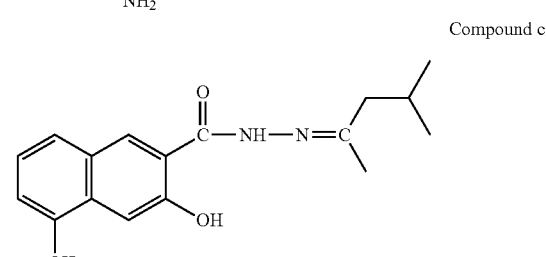

Compound d

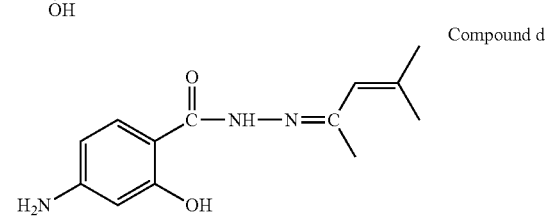

Compound e

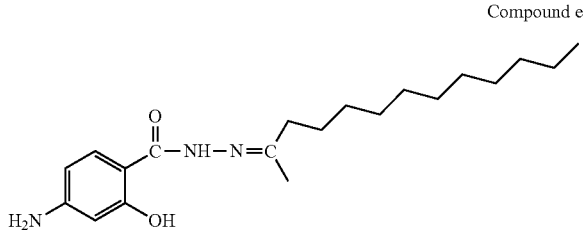

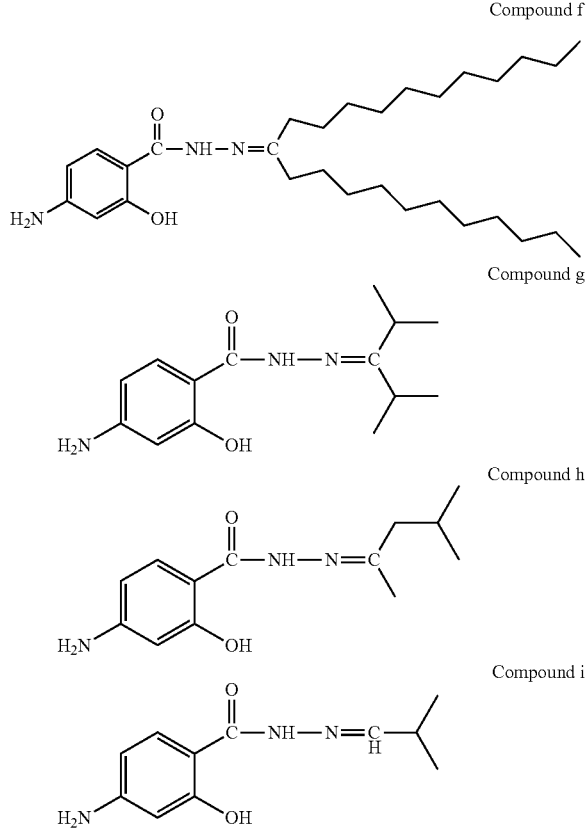

Compound f

Compound g

Compound h

Compound i

The hydrazone compound represented by the Formula (I) contained in the additive for rubber according to the present disclosure can be produced, for example, by a method represented by the following Reaction Formula-1:

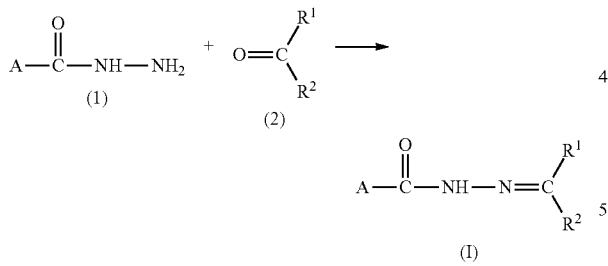

(Reaction Formula-1)

where $R^{1-}$, $R^2$, and A are the same as above.

According to the Reaction Formula-1, the hydrazone compound represented by the Formula (I) can be produced by causing a hydrazide compound represented by the Formula (1) to react on aldehyde or ketone represented by the Formula (2).

This reaction can be performed in a solvent. As the solvent, any known solvents inactive against the reaction can be widely used. Examples include ether-based solvents such as dimethyl ether, diethyl ether, diisopropyl ether, tert-butylmethyl ether, tetrahydrofuran, dioxane, tetrahydropyran, and 1,2-dimethoxyethane, aromatic solvents such as toluene, xylene, and benzene, alcohol-based solvents such as methanol, ethanol, n-propanol, isopropyl alcohol, n-butanol, isobutyl alcohol, sec-butyl alcohol, and tert-butyl alcohol, and water.

The amount of such solvent used is typically about 0.1 parts to 500 parts by mass and preferably about 1 part to 10 parts by mass with respect to 1 part by mass of the hydrazide compound represented by the Formula (1).

The amount of the aldehyde or ketone compound represented by the Formula (2) used in the reaction is typically 0.8 to 10 equivalents and preferably 1 to 2 equivalents with respect to the hydrazide compound represented by the Formula (1).

A catalyst may be used in the reaction. Examples of usable catalysts include mineral acids such as sulfuric acid and hydrochloric acid, organic acids such as formic acid and acetic acid, and organic acid salts such as ammonium formate and ammonium acetate. The amount of such acid catalyst used is typically 0.01 to 0.5 equivalents and preferably 0.01 to 0.2 equivalents with respect to the hydrazide compound represented by the Formula (1).

The reaction can be made typically in a range from about −10° C. to the boiling point of the solvent used. The reaction temperature is typically about 0° C. to 70° C., and preferably about room temperature to 50° C.

The reaction time differs depending on the reaction temperature and the like, but typically the reaction is complete in about 0.5 hr to 24 hr.

The additive for rubber according to the present disclosure may be composed solely of the hydrazone compound represented by the Formula (I), or contain known additives, fillers, other components within the range in which the effects of the hydrazone compound are not hampered.

The amount of the additive for rubber according to the present disclosure added to or blended with the diene-based rubber component is adjusted so that the hydrazone compound represented by the Formula (I) is 0.05 parts to 30 parts by mass with respect to 100 parts by mass of the diene-based rubber component. The hydrazone compound is preferably 0.05 parts to 10 parts by mass and particularly preferably 0.05 parts to 5 parts by mass, with respect to 100 parts by mass of the diene-based rubber component.

The additive for rubber according to the present disclosure is preferably added to the diene-based rubber component using by a mixer, an extruder, a kneader, or spraying.

(Rubber Composition)

A rubber composition according to the present disclosure contains a rubber component, a filler, and an additive for rubber containing a hydrazone compound represented by the following Formula (I):

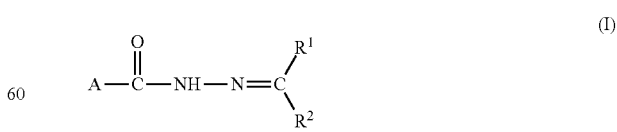

(I)

where $R^1$ and $R^2$ each independently represent a hydrogen atom, an alkyl group with a carbon number of 1 to 16, or an alkenyl group with a carbon number of 2 to 6, and A represents a group represented by the following Formula (A-1) or Formula (A-2):

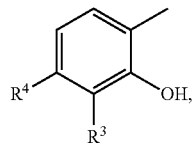
(A-1)

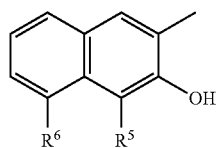
(A-2)

where $R^3$, $R^4$, $R^5$, and $R^6$ each independently represent a hydrogen atom, a hydroxy group, a group of —N($R^7$)($R^8$), or a nitro group, $R^7$ and $R^8$ each independently represent a hydrogen atom, an alkyl group with a carbon number of 1 to 4, or an acyl group with a carbon number of 1 to 4, not both $R^3$ and $R^4$ are a hydrogen atom, and not both $R^5$ and $R^6$ are a hydrogen atom.

Rubber Component

The rubber component contained in the rubber composition according to the present disclosure is not limited as long as it contains diene-based rubber.

Examples of the diene-based rubber include natural rubber, polyisoprene rubber (IR), styrene-butadiene copolymer rubber (SBR), and polybutadiene rubber (BR). Among them, natural rubber is preferable, because better low heat generating property and processability can be achieved.

One of these diene-based rubbers may be used, or a blend of two or more of these diene-based rubbers may be used.

The content of the diene-based rubber in the rubber component is not limited. In terms of maintaining excellent low heat generating property, the content of the diene-based rubber is preferably 80 mass % or more, and more preferably 90 mass % or more.

Filler

The rubber composition according to the present disclosure contains a filler in addition to the above-described rubber component.

By containing the filler together with the rubber component and the below-described compound represented by the Formula (I), excellent low heat generating property and processability can be achieved without decreasing other properties.

The content of the filler is not limited, but is preferably 10 parts to 160 parts by mass and more preferably 30 parts to 100 parts by mass with respect to 100 parts by mass of the rubber component. With appropriate content of the filler, better low heat generating property and processability can be achieved. If the content is less than 10 parts by mass, sufficient fracture resistance may not be obtained. If the content is more than 160 parts by mass, sufficient low heat generating property may not be obtained.

The type of the filler is not limited. Examples include carbon black, silica, and other inorganic fillers. Among them, the filler preferably includes carbon black, because better low heat generating property and processability can be achieved.

Examples of the carbon black include carbon black of GPF, FEF, SRF, HAF, ISAF, IISAF, and SAF grade.

Examples of the silica include wet silica, dry silica, and colloidal silica.

Examples of the other inorganic fillers include an inorganic compound represented by the following Formula (II):

$$nM.xSiO_Y.zH_2O \qquad (II)$$

(where M is at least one selected from metals selected from the group consisting of aluminum, magnesium, titanium, calcium, and zirconium, oxides or hydroxides of these metals, hydrates thereof, and carbonates of these metals, and n, x, y, and z are an integer of 1 to 5, an integer of 0 to 10, an integer of 2 to 5, and an integer of 0 to 10 respectively.)

Examples of the inorganic compound represented by the Formula (II) include: alumina ($Al_2O_3$) such as γ-alumina and α-alumina; alumina monohydrate ($Al_2O_3.H_2O$) such as boehmite and diaspore; aluminum hydroxide [$Al(OH)_3$] such as gibbsite and bayerite; and aluminum carbonate [$Al_2(CO_3)_3$], magnesium hydroxide [$Mg(OH)_2$], magnesium oxide (MgO), magnesium carbonate ($MgCO_3$), talc ($3MgO.4SiO_2.H_2O$), attapulgite ($5MgO.8SiO_2.9H_2O$), titanium white ($TiO_2$), titanium black ($TiO_{2n-1}$), calcium oxide (CaO), calcium hydroxide [$Ca(OH)_2$], aluminum magnesium oxide ($MgO.Al_2O_3$), clay ($Al_2O_3.2SiO_2$), kaolin ($Al_2O_3.2SiO_2.2H_2O$), pyrophyllite ($Al_2O_3.4SiO_2.H_2O$), bentonite ($Al_2O_3.4SiO_2.2H_2O$), aluminum silicate ($Al_2SiO_5$, $Al_4.3SiO_4.5H_2O$, etc.), magnesium silicate ($Mg_2SiO_4$, $MgSiO_3$, etc.), calcium silicate ($Ca_2SiO_4$, etc.), aluminum calcium silicate ($Al_2O_3.CaO.2SiO_2$, etc.), magnesium calcium silicate ($CaMgSiO_4$), calcium carbonate ($CaCO_3$), zirconium oxide ($ZrO_2$), zirconium hydroxide [$ZrO(OH)_2.nH_2O$], zirconium carbonate [$Zr(CO_3)_2$], and crystalline aluminosilicate containing hydrogen, alkali metal, or alkaline earth metal that corrects electric charge like various zeolites.

Additive for Rubber

The rubber composition according to the present disclosure contains the above-described additive for rubber according to the present disclosure.

The group A-1 or group A-2 represented by A in the hydrazone compound represented by the Formula (I) has high affinity for the filler such as carbon black, and the part having hydrazone moiety in the hydrazone compound has high affinity for the rubber component. Therefore, the additive for rubber, as a result of being blended with the rubber composition, can significantly improve chemical interaction between the rubber component and the filler. This can reduce hysteresis caused by friction between fillers, so that very good low heat generating property can be achieved as compared with conventional techniques. In addition, improvement in the dispersibility of the filler contributes to better reinforcement.

As a result of significantly improving chemical interaction between the rubber component and the filler, the unvulcanized viscosity can be decreased while maintaining the low heat generating property of the rubber composition. Thus, processability can also be improved.

Regarding the content of the additive for rubber in the rubber composition according to the present disclosure, the hydrazone compound represented by the Formula (I) is preferably 0.05 parts to 30 parts by mass, more preferably 0.05 parts to 10 parts by mass, and further preferably 0.05 parts to 5 parts by mass with respect to 100 parts by mass of the rubber component. By setting the content to 0.05 parts by mass or more with respect to 100 parts by mass of the rubber component, desired low heat generating property and processability can be achieved. By setting the content to 30 parts by mass or less with respect to 100 parts by mass of the rubber component, processability and other properties such as strength can be maintained favorably.

Other Components

The rubber composition according to the present disclosure may contain, in addition to the rubber component, the filler, and the additive for rubber, compounding agents commonly used in the rubber industry, which are selected as appropriate within the range in which the object of the present disclosure is not hampered. Examples of a such compounding agent include an antioxidant, a softener, a silane coupling agent, a stearic acid, a zinc oxide, a resin, a vulcanization accelerator, and a vulcanizing agent. Commercial products are suitable for use as these compounding agents.

The production method for the rubber composition according to the present disclosure is not limited. For example, the rubber composition can be yielded by blending and kneading the rubber component containing diene-based rubber, the filler, and the additive containing the hydrazone compound represented by the Formula (I) by a known method.

(Tire)

A tire according to the present disclosure is formed using the above-described rubber composition according to the present disclosure. With the inclusion of the rubber composition according to the present disclosure as tire material, excellent low heat generating property can be achieved without decreasing other properties.

The part in which the rubber composition is used in the tire is preferably the tread. The tire with the rubber composition according to the present disclosure used in its tread has excellent low heat generating property.

The tire according to the present disclosure is not limited as long as the above-described rubber composition according to the present disclosure is used in any of its tire members, and can be produced according to conventional methods. As a gas with which the tire is filled, an inert gas such as nitrogen, argon, or helium can be used as well as normal air or air whose oxygen partial pressure has been adjusted.

(Hydrazone Compound)

A hydrazone compound according to the present disclosure is represented by the following Formula (I):

$$A-\overset{O}{\underset{\|}{C}}-NH-N=C\overset{R^1}{\underset{R^2}{\diagdown}}$$

(I)

where $R^1$ and $R^2$ each independently represent a hydrogen atom, an alkyl group with a carbon number of 1 to 16, or an alkenyl group with a carbon number of 2 to 6, and A represents a group represented by the following Formula (A-1) or Formula (A-2):

(A-1)

(A-2)

where $R^3$, $R^4$, $R^5$, and $R^6$ each independently represent a hydrogen atom, a hydroxy group, a group of $-N(R^7)(R^8)$, or a nitro group, $R^7$ and $R^8$ each independently represent a hydrogen atom, an alkyl group with a carbon number of 1 to 4, or an acyl group with a carbon number of 1 to 4, not both $R^3$ and $R^4$ are a hydrogen atom, and not both $R^5$ and $R^6$ are a hydrogen atom.

As a result of the hydrazone compound being contained in the above-described additive for rubber according to the present disclosure, the low heat generating property and processability of the rubber composition can be improved.

EXAMPLES

More detailed description will be given below by way of production examples and examples, although the present disclosure is not limited to these production examples and examples.

Production Example 1

Production of 2,3-dihydroxy-N'-(4-methylpentan-2-ylidene)benzohydrazide (Compound a)

1.20 g of 2,3-dihydroxybenzohydrazide and 3.00 g of methyl isobutyl ketone were added to 10.0 mL of methanol, and stirred at 65° C. for 12 hr. The reaction mixture was concentrated and diisopropyl ether was added to the precipitated solid. The precipitated solid was then filtered, and further washed with diisopropyl ether. The resultant solid was dried under reduced pressure, thus obtaining 1.61 g of a pale yellow solid 2,3-dihydroxy-N'-(4-methylpentan-2-ylidene)benzohydrazide (yield: 90%). The melting point and $^1$H-NMR of the obtained compound are as follows:

Melting point: 138° C.

$^1$H-NMR (300 MHz, DMSO-$d_6$, δppm): 0.91 (m, 6H), 2.0 (m, 4H), 2.2 (m, 2H), 6.8 (m, 1H), 7.0 (m, 1H), 7.4 (m, 1H), 9.6 (m, 1H), 10.9 (m, 1H), 11.2 (m, 1H).

Production Example 2

Production of 4-amino-3-hydroxy-N'-(4-methylpentan-2-ylidene)naphthalene-2-carbohydrazide (Compound b)

39.7 g of 4-amino-3-hydroxy-2-naphthoic acid hydrazide and 36.6 g of methyl isobutyl ketone were added to 183 mL of methanol, and stirred at 65° C. for 3 hr. The reaction mixture was cooled, and the precipitated solid was filtered and washed with isopropyl alcohol. The resultant solid was dried under reduced pressure, thus obtaining 52.1 g of a pale yellow solid 4-amino-3-hydroxy-N'-(4-methylpentan-2-ylidene)naphthalene-2-carbohydrazide (yield: 95%). The melting point and ¹H-NMR of the obtained compound are as follows:

Melting point: 166° C.

¹H-NMR (300 MHz, DMSO-d₆, δppm): 0.93 (m, 6H), 2.0 (m, 4H), 2.2 (m, 2H), 7.3 (m, 2H), 7.4 (m, 2H), 7.8 (m, 2H), 8.0 (m, 1H), 11.1 (m, 1H), NH (2H) was not detected.

Production Example 3

Production of 3,5-dihydroxy-N'-(4-methylpentan-2-ylidene)naphthalene-2-carbohydrazide (Compound c)

2.85 g of 3,5-dihydroxy-2-naphthoic acid hydrazide and 2.76 g of methyl isobutyl ketone were added to 12.0 mL of methanol, and stirred at 65° C. for 4 hr. The reaction mixture was concentrated, and diisopropyl ether was added to the precipitated solid. The precipitated solid was then filtered, and further washed with diisopropyl ether. The resultant solid was dried under reduced pressure, thus obtaining 3.84 g of a pale yellow solid 3,5-dihydroxy-N'-(4-methylpentan-2-ylidene)naphthalene-2-carbohydrazide (yield: 98%). The melting point and ¹H-NMR of the obtained compound are as follows:

Melting point: 130° C.

¹H-NMR (300 MHz, DMSO-d₆, δppm): 0.94 (m, 6H), 2.0 (m, 4H), 2.2 (m, 2H), 6.8 (m, 1H), 7.1 (m, 1H), 7.4 (m, 1H), 7.6 (m, 1H), 8.5 (m, 1H), 10.1 (s, 1H), 11.2 (m, 1H), 11.6 (m, 1H).

Production Example 4

Production of 4-amino-2-hydroxy-N'-(4-methyl-penta-3-en-2-ylidene)benzohydrazide (Compound d)

4.73 g of 4-amino-2-hydroxybenzohydrazide and 3.34 g of 4-methylpenta-3-en-2-one were added to 50.0 mL of methanol, and stirred at 65° C. for 1 hr. The reaction mixture was cooled, and the precipitated solid was filtered and washed with methanol. The resultant solid was dried under reduced pressure, thus obtaining 3.01 g of a pale yellow solid 4-amino-2-hydroxy-N'-(4-methylpenta-3-en-2-ylidene)benzohydrazide (yield: 43%). The melting point and ¹H-NMR of the obtained compound are as follows:

Melting point: 176° C.

¹H-NMR (300 MHz, DMSO-d₆, δppm): 1.6 (m, 3H), 1.9 (m, 3H), 2.0 (m, 3H), 5.6 (m, 1H), 5.7 (m, 2H), 6.08 (m, 1H), 6.13 (m, 1H), 7.6 (m, 1H), 10.9 (m, 2H).

Production Example 5

Production of 4-amino-2-hydroxy-N'-(tridecan-2-ylidene)benzohydrazide (Compound e)

4.81 g of 4-amino-2-hydroxybenzohydrazide and 6.85 g of tridecane-2-one were added to 50.0 mL of methanol, and stirred at 65° C. for 1 hr. The reaction mixture was concentrated, and isopropyl alcohol was added to the precipitated solid. The precipitated solid was then filtered, and further washed with isopropyl alcohol. The resultant solid was dried under reduced pressure, thus obtaining 8.18 g of a pale yellow solid 4-amino-2-hydroxy-N'-(tridecan-2-ylidene)benzohydrazide (yield: 82%). The melting point and ¹H-NMR of the obtained compound are as follows:

Melting point: 155° C.

¹H-NMR (500 MHz, DMSO-d₆, δppm): 0.86 (m, 3H), 1.3 (m, 16H), 1.5 (m, 2H), 1.9 (m, 3H), 2.3 (m, 2H), 5.8 (m, 2H), 6.1 (m, 2H), 7.6 (m, 1H), 10.5 (m, 1H), 11.6 (m, 1H).

Production Example 6

Production of 4-amino-2-hydroxy-N'-(tricosan-12-ylidene)benzohydrazide (Compound f)

4.80 g of 4-amino-2-hydroxybenzohydrazide and 9.72 g of tricosan-12-one were added to 50.0 mL of methanol, and stirred at 65° C. for 1 hr. The reaction mixture was cooled, and the precipitated solid was filtered and washed with methanol. The resultant solid was dried under reduced pressure, thus obtaining 11.1 g of a pale yellow solid 4-amino-2-hydroxy-N'-(tricosan-12-ylidene)benzohydrazide (yield: 79%). The melting point and ¹H-NMR of the obtained compound are as follows:

Melting point: 151° C.

¹H-NMR (300 MHz, DMSO-d₆, δppm): 0.86 (m, 6H), 1.2 (m, 32H), 1.5 (m, 4H), 2.3 (m, 4H), 5.8 (br-s, 2H), 6.1 (m, 2H), 7.6 (m, 1H), 10.7 (br-s, 1H), 11.5 (br-s, 1H).

Production Example 7

Production of 4-amino-N'-(2,4-dimethylpentan-3-ylidene)-2-hydroxybenzohydrazide (Compound g)

4.45 g of 4-amino-2-hydroxybenzohydrazide and 64.0 g of diisopropyl ketone were added to 50.0 mL of methanol, and stirred at 65° C. for 48 hr. The reaction mixture was cooled, and the precipitated solid was filtered and washed with methanol. The resultant solid was purified by silica gel column chromatography, thus obtaining 5.25 g of a pale yellow solid 4-amino-N'-(2,4-dimethylpentan-3-ylidene)-2-hydroxybenzohydrazide (yield: 75%). The melting point and ¹H-NMR of the obtained compound are as follows:

Melting point: 162° C.

¹H-NMR (300 MHz, DMSO-d₆, δppm): 1.1 (m, 12H), 2.7 (m, 1H), 3.0 (m, 1H), 5.7 (br-s, 2H), 6.1 (m, 2H), 7.6 (d, 1H), 10.7 (br-s, 1H), 11.6 (br-s, 1H).

Production Example 8

Production of 4-amino-2-hydroxy-N'-(4-methylpentan-2-ylidene)benzohydrazide (Compound h)

1.66 g of 4-amino-2-hydroxybenzohydrazide and 1.05 g of methyl isobutyl ketone were added to 20.0 mL of methanol, and stirred at 65° C. for 2 hr. 20.0 mL of diisopropyl ether was added to the reaction mixture, and the precipitated solid was filtered and further washed with diisopropyl ether. The resultant solid was dried under reduced pressure, thus obtaining 1.59 g of a pale yellow solid 4-amino-2-hydroxy-N'-(4-methylpentan-2-ylidene)benzohydrazide (yield: 64%). The melting point and ¹H-NMR of the obtained compound are as follows:

Melting point: 203° C.

¹H-NMR (300 MHz, DMSO-d₆, δppm): 0.91 (m, 6H), 2.0 (m, 4H), 2.2 (m, 2H), 5.7 (m, 2H), 6.1 (m, 2H), 7.6 (m, 1H), 10.6 (m, 1H), 11.6 (m, 1H).

Production Example 9

Production of 4-amino-2-hydroxy-N'-(2-methylpropylidene)benzohydrazide (Compound i)

5.29 g of 4-amino-2-hydroxybenzohydrazide and 2.74 g of isobutylaldehyde were added to 50.0 mL of methanol, and stirred at 65° C. for 1 hr. The precipitated solid was filtered, and then washed with diisopropyl ether. The resultant solid was purified by silica gel column chromatography, thus obtaining 4.00 g of a pale yellow solid 4-amino-2-hydroxy-N'-(2-methylpropylidene)benzohydrazide (yield: 57%). The melting point and $^1$H-NMR of the obtained compound are as follows:

Melting point: 95° C.

$^1$H-NMR (300 MHz, DMSO-$d_6$, δppm): 1.1 (m, 6H), 2.5 (m, 1H), 5.9 (br-s, 2H), 6.0 (m, 1H), 6.1 (m, 1H), 7.6 (m, 2H), 11.1 (br-s, 1H), 12.6 (br-s, 1H).

Examples 1 to 9 and Comparative Examples 1 and 2

Rubber compositions of formulations listed in Table 1 were prepared by kneading using Plastomill.

The low heat generating property and processability of each prepared rubber composition were evaluated by the following methods.

The evaluation results are listed in Table 1.

(1) Tan δ (Low Heat Generating Property)

The rubber composition of each sample was vulcanized at 145° C. for 33 min to obtain vulcanized rubber. The loss tangent (tan δ) of the obtained vulcanized rubber was measured at a temperature of 50° C., a strain of 5%, and a frequency of 15 Hz, using a viscoelasticity measuring instrument (produced by Rheometric Scientific).

tan δ is represented by an index with the value of Comparative Example 1 being 100, and a smaller index value indicates better low heat generating property.

(2) Unvulcanized Viscosity (Processability)

The unvulcanized viscosity of the rubber composition of each sample was measured by a Mooney viscosity test at 100° C. in accordance with JIS K 6300-1.

The unvulcanized viscosity is represented by an index with the value of Comparative Example 1 being 100, and a smaller index value indicates lower viscosity and easier unvulcanized rubber molding.

TABLE 1

| | | Example | | | | | | | | | Comparative Example | |
|---|---|---|---|---|---|---|---|---|---|---|---|---|
| | | 1 | 2 | 3 | 4 | 5 | 6 | 7 | 8 | 9 | 1 | 2 |
| Formulation (parts by mass) | Natural rubber*[1] | 100 | 100 | 100 | 100 | 100 | 100 | 100 | 100 | 100 | 100 | 100 |
| | Carbon black N220*[2] | 50 | 50 | 50 | 50 | 50 | 50 | 50 | 50 | 50 | 50 | 50 |
| | Compound a*[9] | 1 | — | — | — | — | — | — | — | — | — | — |
| | Compound b*[9] | — | 1 | — | — | — | — | — | — | — | — | — |
| | Compound c*[9] | — | — | 1 | — | — | — | — | — | — | — | — |
| | Compound d*[9] | — | — | — | 1 | — | — | — | — | — | — | — |
| | Compound e*[9] | — | — | — | — | 1 | — | — | — | — | — | — |
| | Compound f*[9] | — | — | — | — | — | 1 | — | — | — | — | — |
| | Compound g*[9] | — | — | — | — | — | — | 1 | — | — | — | — |
| | Compound h*[9] | — | — | — | — | — | — | — | 1 | — | — | — |
| | Compound f*[9] | — | — | — | — | — | — | — | — | 1 | — | — |
| | Compound j*[3] | — | — | — | — | — | — | — | — | — | 1 | — |
| | Compound k*[4] | — | — | — | — | — | — | — | — | — | — | 1 |
| | Aromatic oil*[5] | 2 | 2 | 2 | 2 | 2 | 2 | 2 | 2 | 2 | 2 | 2 |
| | Stearic acid | 2 | 2 | 2 | 2 | 2 | 2 | 2 | 2 | 2 | 2 | 2 |
| | Antioxidant 6PPD*[6] | 1 | 1 | 1 | 1 | 1 | 1 | 1 | 1 | 1 | 1 | 1 |
| | Antioxidant TMQ*[7] | 1 | 1 | 1 | 1 | 1 | 1 | 1 | 1 | 1 | 1 | 1 |
| | Zinc oxide | 3 | 3 | 3 | 3 | 3 | 3 | 3 | 3 | 3 | 3 | 3 |
| | Vulcanization accelerator CBS*[8] | 0.8 | 0.8 | 0.8 | 0.8 | 0.8 | 0.8 | 0.8 | 0.8 | 0.8 | 0.8 | 0.8 |
| | Sulfur | 1.5 | 1.5 | 1.5 | 1.5 | 1.5 | 1.5 | 1.5 | 1.5 | 1.5 | 1.5 | 1.5 |
| Evaluation | tanδ index (low heat generating property) | 87 | 83 | 88 | 93 | 96 | 97 | 99 | 98 | 99 | 100 | 90 |
| | Unvulcanized viscosity index (processability) | 99 | 94 | 95 | 81 | 88 | 82 | 81 | 93 | 95 | 100 | 115 |

*[1]RSS #1

*[2]"#80" produced by Asahi Carbon Co., Ltd.

*[3]3-hydroxy-2-naphthoic acid hydrazide, produced by Tokyo Chemical Industry Co., Ltd.

*[4]isophthalic dihydrazide, produced by Tokyo Chemical Industry Co., Ltd.

*[5]"AROMAX#3" produced by Fuji Kosan Co., Ltd.

*[6]N-(1,3-dimethylbutyl)-N'-phenyl-p-phenylenediamine, product name "NOCRAC 6C" produced by Ouchi Shinko Chemical Industrial Co., Ltd.

*[7]2,2,4-trimethyl-1,2-dihydroquinoline polymer, product name "NOCRAC 224" produced by Ouchi Shinko Chemical Industrial Co., Ltd.

*[8]N-cyclohexyl-2-benzothiazolesulfenamide, "SANCELER CM" produced by Sanshin Chemical Industry Co. Ltd.

*[9]Compounds a to i obtained according to Production Examples 1 to 9.

As can be seen from the results in Table 1, the rubber composition of each Example exhibited better low heat generating property and processability than the rubber composition of Comparative Example 1. Moreover, the rubber composition of each of Examples 1 to 3 exhibited better low heat generating property and processability than the rubber composition of Comparative Example 2.

INDUSTRIAL APPLICABILITY

It is thus possible to provide an additive for rubber that can improve the low heat generating property and processability of a rubber composition, and a rubber composition having excellent low heat generating property and processability. It is also possible to provide a tire having excellent low heat generating property.

The invention claimed is:

1. A rubber composition comprising:
a rubber component containing diene-based rubber;
a filler; and
an additive for rubber, comprising
a hydrazone compound of at least one selected from Compound b to Compound i.

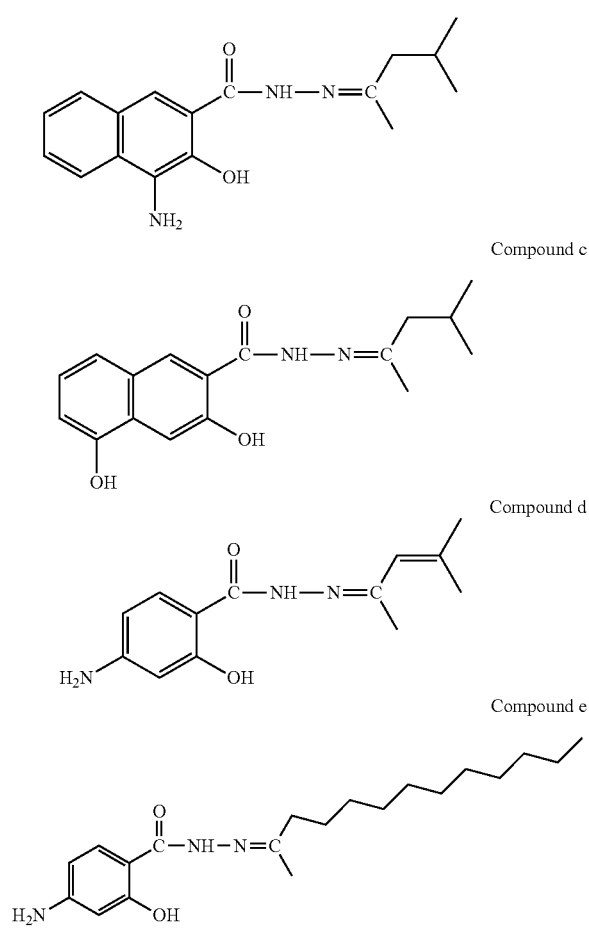

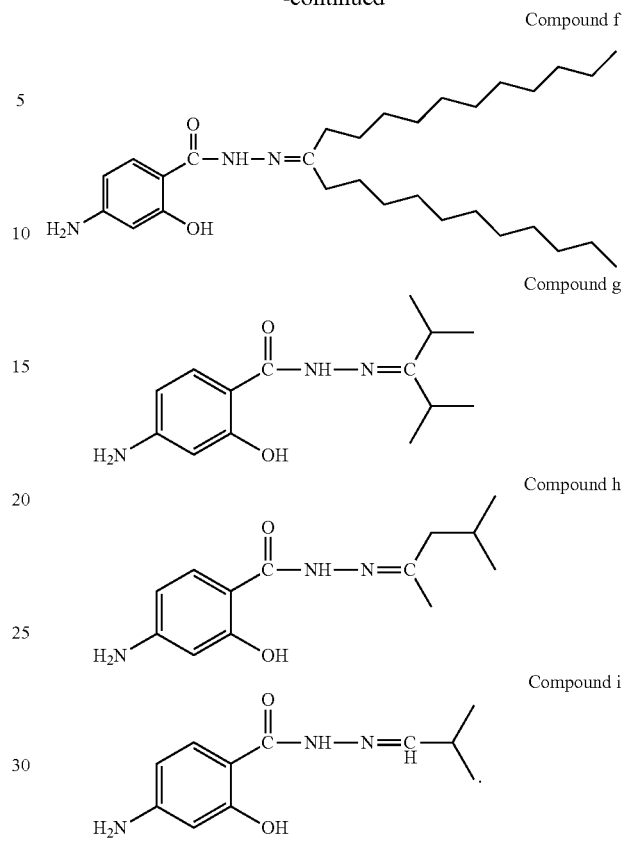

2. The rubber composition according to claim 1, wherein a content of the filler is 10 parts to 160 parts by mass with respect to 100 parts by mass of the rubber component.

3. The rubber composition according to claim 1, wherein the filler includes carbon black.

4. The rubber composition according to claim 3, wherein a content of the filler is 10 parts to 160 parts by mass with respect to 100 parts by mass of the rubber component.

5. The rubber composition according to claim 1, wherein the diene-based rubber is natural rubber.

6. The rubber composition according to claim 5, wherein the filler includes carbon black.

7. The rubber composition according to claim 5, wherein a content of the filler is 10 parts to 160 parts by mass with respect to 100 parts by mass of the rubber component.

8. The rubber composition according to claim 1, wherein a content of the additive for rubber is 0.05 parts to 30 parts by mass with respect to 100 parts by mass of the rubber component.

9. The rubber composition according to claim 8, wherein the diene-based rubber is natural rubber.

10. The rubber composition according to claim 8, wherein the filler includes carbon black.

11. The rubber composition according to claim 8, wherein a content of the filler is 10 parts to 160 parts by mass with respect to 100 parts by mass of the rubber component.

12. A tire comprising
the rubber composition according to claim 1.

* * * * *